US011364629B2

(12) United States Patent
Sefati et al.

(10) Patent No.: US 11,364,629 B2
(45) Date of Patent: Jun. 21, 2022

(54) DATA-DRIVEN POSITION ESTIMATION AND COLLISION DETECTION FOR FLEXIBLE MANIPULATOR

(71) Applicant: The Johns Hopkins University, Baltimore, MD (US)

(72) Inventors: Shahriar Sefati, Baltimore, MD (US); Mehran Armand, Maple Lawn, MD (US); Iulian Iordachita, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 354 days.

(21) Appl. No.: 16/801,272

(22) Filed: Feb. 26, 2020

(65) Prior Publication Data

US 2020/0338723 A1    Oct. 29, 2020

Related U.S. Application Data

(60) Provisional application No. 62/839,624, filed on Apr. 27, 2019.

(51) Int. Cl.
*B25J 9/16*    (2006.01)
*B25J 9/10*    (2006.01)
(Continued)

(52) U.S. Cl.
CPC ............ *B25J 9/163* (2013.01); *B25J 9/104* (2013.01); *B25J 9/1666* (2013.01); *B25J 9/1697* (2013.01); *B25J 18/06* (2013.01); *B25J 19/025* (2013.01)

(58) Field of Classification Search
CPC . B25J 9/163; B25J 9/104; B25J 9/1666; B25J 9/1697; B25J 18/06; B25J 19/025;
(Continued)

(56) References Cited

U.S. PATENT DOCUMENTS 6,648,640 B2 * 11/2003 Rubbert ................. G16H 50/50
433/24
8,121,718 B2 * 2/2012 Rubbert ................. G06T 17/00
700/98
(Continued)

FOREIGN PATENT DOCUMENTS

WO    2018037931    3/2018
WO    2019170787    9/2019

OTHER PUBLICATIONS

Michael C. Yip, et al., "Model-Less Hybrid Position/Force Control: A Minimalist Approach for Continuum Manipulators in Unknown, Constrained Environments," IEEE Robotics and Automation Letters, vol. 1, No. 2, 844-651, Jul. 2016.
(Continued)

*Primary Examiner* — Jaime Figueroa
(74) *Attorney, Agent, or Firm* — Noah J. Hayward (57) ABSTRACT

A flexible manipulator apparatus includes an elongate flexible manipulator having a sensor, a user output device configured to provide sensory outputs to the user, and processing circuitry. The flexible manipulator may be movable to form a curve in the flexible manipulator. The processing circuitry may be configured to receive captured sensor data from the sensor during movement of the flexible manipulator, and determine a collision likelihood score based on application of the captured sensor data to a collision detection model used for position estimation. The collision detection model may be based on an empirical data training for the flexible manipulator that includes training sensor data from the sensor and training image data of positions of the flexible manipulator. The processing circuitry may be configured to control the user output device based on the collision likelihood score to provide a collision alert sensory output to the user.

20 Claims, 7 Drawing Sheets

(51) Int. Cl.
B25J 18/06 (2006.01)
B25J 19/02 (2006.01)

(58) Field of Classification Search
CPC ........ B25J 9/1676; A61B 34/20; A61B 34/25; A61B 34/74; A61B 90/361; A61B 34/30; G05B 2219/39082; G05B 2219/40279
USPC .................................................. 700/245–264
See application file for complete search history.

(56) References Cited

U.S. PATENT DOCUMENTS

| | | | |
|---|---|---|---|
| 8,989,528 B2* | 3/2015 | Udd | A61B 5/065 385/13 |
| 9,333,044 B2* | 5/2016 | Olson | A61B 34/32 |
| 9,333,650 B2 | 5/2016 | Bajo et al. | |
| 9,693,707 B2* | 7/2017 | Chan | A61B 5/061 |
| 10,111,723 B2* | 10/2018 | Olson | A61B 34/37 |
| 10,299,773 B2 | 5/2019 | Frimer et al. | |
| 10,300,599 B2 | 5/2019 | Simaan et al. | |
| 10,846,928 B2* | 11/2020 | Alterovitz | A61B 1/2676 |
| 10,967,504 B2* | 4/2021 | Simaan | B25J 9/161 |
| 11,045,958 B2* | 6/2021 | Bowling | B25J 13/00 |
| 11,179,210 B2* | 11/2021 | Bowling | B25J 9/009 |
| 11,291,510 B2* | 4/2022 | Shelton, IV | A61B 17/1155 |
| 2001/0021843 A1* | 9/2001 | Bosselmann | A61B 1/009 606/2 |
| 2002/0015934 A1* | 2/2002 | Rubbert | A61C 7/146 433/29 |
| 2003/0096210 A1* | 5/2003 | Rubbert | G06T 17/00 433/24 |
| 2007/0156019 A1* | 7/2007 | Larkin | B25J 9/1635 600/104 |
| 2008/0065110 A1* | 3/2008 | Duval | A61B 34/72 606/130 |
| 2008/0302200 A1* | 12/2008 | Tobey | B25J 18/06 901/14 |
| 2009/0291417 A1* | 11/2009 | Rubbert | A61C 9/0046 703/11 |
| 2010/0030063 A1* | 2/2010 | Lee | A61B 5/06 600/424 |
| 2011/0230894 A1* | 9/2011 | Simaan | A61B 1/018 606/130 |
| 2013/0310685 A1* | 11/2013 | Chan | A61B 34/20 600/424 |
| 2015/0005785 A1* | 1/2015 | Olson | G16H 40/67 901/9 |
| 2016/0324587 A1* | 11/2016 | Olson | A61B 34/32 |
| 2017/0312920 A1 | 11/2017 | Yip et al. | |
| 2018/0271603 A1 | 9/2018 | Nir et al. | |

OTHER PUBLICATIONS

David Jakes, et al., "Model-less Active Compliance for Continuum Robots using Recurrent Neural Networks," Cornell University, arXiv:1902.08943v1 [cs.RO], available online at https://arxiv.org/abs/1902.08943, pp. 1-7, Feb. 24, 2019.

Michael C. Yip, et al., "Model-Less Feedback Control of Continuum Manipulators in Constrained Environments," IEEE Transactions on Robotics, vol. 30, No. 4, pp. 880-889, Aug. 2014.

Kit-Hang Lee, et al., "Nonparametric Online Learning Control for Soft Continuum Robot: An Enabling Technique for Effective Endoscopic Navigation," Soft Robotics, vol. 4, No. 4, pp. 324-337, 2017.

Thomas George Thuruthel, et al., "Learning Closed Loop Kinematic Controllers for Continuum Manipulators in Unstructured Environments," Soft Robotics, vol. 4, No. 3, pp. 285-296, 2017.

Peng Qi, et al., "Kinematic Control of Continuum Manipulators Using a Fuzzy-Model-Based Approach," IEEE Transactions on Industrial Electronics, vol. 63, No. 8, pp. 5022-5035, Aug. 2016.

Sreeshankar Satheeshbabu, et al., "Open Loop Position Control of Soft Continuum Arm Using Deep Reinforcement Learning," 2019 International Conference on Robotics and Automation (ICRA), Palais des congres de Montreal, Montreal, Canada, pp. 5133-5139, May 20, 2019.

\* cited by examiner

DATA-DRIVEN POSITION ESTIMATION AND COLLISION DETECTION FOR FLEXIBLE MANIPULATOR

CROSS-REFERENCE TO RELATED APPLICATIONS

This application claims priority to and the benefit of prior-filed, co-pending U.S. Provisional Application No. 62/839,624 filed on Apr. 27, 2019, the entire contents of which are hereby incorporated herein by reference.

STATEMENT OF GOVERNMENTAL INTEREST

This invention was made with Government support under contract number R01EB016703-01A1 awarded by the National Institutes of Health (NIH). The Government has certain rights in the invention.

TECHNICAL FIELD

Exemplary embodiments of the present disclosure generally relate to implementation of flexible manipulators, and more specifically relate to implementation of techniques for flexible manipulators to estimate position and avoid environmental collisions.

BACKGROUND

Due to their flexibility, dexterity, and compact size, continuum manipulators (CMs) can enhance minimally invasive interventions, particularly in the medical arena. In these procedures, the CM may be operated in proximity of sensitive organs and other tissue. Collisions by the CM can damage such organs or tissue, and therefore avoidance of such collisions can be of paramount concern when conducting invasive procedures. Conventional CM models, which may be used in association with collision avoidance, use complex characteristic information for the type of CM device based on architectural characteristics, movement characteristics, and a priori information about the CM. Such conventional models are complicated to generate and may not accurately represent the movement characteristics of a particular CM. As such, more simplified and accurate approaches to generation of models used for collision detection are needed that are not specific to an individual CM.

BRIEF SUMMARY OF SOME EXAMPLES

According to some example embodiments, a flexible manipulator apparatus is provided. The flexible manipulator apparatus may comprise an elongate flexible manipulator comprising a sensor. The flexible manipulator may be movable to form a curve in the flexible manipulator. Further, the flexible manipulator apparatus may comprise a user output device configured to provide sensory outputs to the user, and the flexible manipulator apparatus may further comprise processing circuitry. The processing circuitry may be configured to receive captured sensor data from the sensor during movement of the flexible manipulator, and determine a collision likelihood score based on application of the captured sensor data to a collision detection model used for position estimation. In this regard, the collision detection model may be based on an empirical data training for the flexible manipulator comprising training sensor data from the sensor and training image data of positions of the flexible manipulator. The processing circuitry may also be configured to control the user output device based on the collision likelihood score to provide a collision alert sensory output to the user.

According to some example embodiments, a system for generating a collision detection model for a flexible manipulator apparatus is provided. The system may comprise an elongate flexible manipulator comprising a sensor. In this regard, the flexible manipulator may be movable to form a curve in the flexible manipulator. The system may further comprise a camera configured capture movement of the flexible manipulator relative to a test collision object, and processing circuitry in communication with the flexible manipulator and the camera. The processing circuitry may be configured to control the flexible manipulator to cause iterations of movement relative to the test collision object, with at least one iteration of movement involving a collision between the flexible manipulator and the test collision object. The processing circuitry may also be configured to receive sensor data sets associated with the iterations of movement of the flexible manipulator from the sensor, receive image data sets associated with the iterations of movement of the flexible manipulator from the camera, synthesize the sensor data sets with the image data sets to classify the iterations of movement into a collision class and a no collision class, and generate the collision detection model for use with the flexible manipulator for position estimation in future procedures based on the synthesized data sets and the classifications of the iterations of movement.

According to some example embodiments, a method for generating a collision detection model for a flexible manipulator apparatus is provided. The method may comprise controlling a flexible manipulator to cause iterations of movement relative to a test collision object with at least one iteration of movement involving a collision between the flexible manipulator and the test collision object, and receiving sensor data sets associated with the iterations of movement of the flexible manipulator from a sensor. In this regard, the flexible manipulator may comprise the sensor. Further, the method may comprise receiving image data sets associated with the iterations of movement of the flexible manipulator from a camera. In this regard, the camera may be remote from the flexible manipulator. Further, the method may include synthesizing, by processing circuitry, the sensor data sets with the image data sets to classify the iterations of movement into a collision class and a no collision class, and generating a collision detection model for use with the flexible manipulator for position estimate in future procedures based on the synthesized data sets and the classifications of the iterations of movement.

BRIEF DESCRIPTION OF THE SEVERAL VIEWS OF THE DRAWING(S)

Having thus described some example embodiments of the invention in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability, or configuration of the present disclosure. Rather, these example embodiments are provided so that this disclosure will satisfy applicable legal requirements. Like reference numerals refer to like elements throughout.

As used herein, the terms "component," "module," and the like are intended to include a computer-related entity, such as but not limited to hardware, firmware, or a combination of hardware and software. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

Compared to conventional rigid-link robots, continuum manipulators (CMs) exhibit higher dexterity, flexibility, compliance, and conformity to confined spaces, making them suitable for minimally invasive interventions. Examples of the use of CMs in medical applications include, but not limited to, neurosurgery, otolaryngology, cardiac, vascular, and abdominal interventions. In such medical applications, the CM may be used for steering in curvilinear pathways, manipulating tissue, or merely as a flexible pathway for navigation of flexible instruments to a desired surgical site, all of which accentuating the necessity of detecting CM collision or contact with bone, tissue, or organs.

According to some example embodiments, a data-driven machine learning approach is described herein using sensory information (and is some instances only sensory information), without requiring any prior geometrical assumptions, architectural or manufacturing model of the CM, or the surrounding environment. In this regard, according to some example embodiments, a non-constant curvature CM, equipped with fiber Bragg grating (FBG) optical sensors for shape sensing purposes may be used in association with a position estimation model to be used for collision detection that is generated based on a data-driven, machine learning approach to successfully detect collisions in constrained environments with soft and hard obstacles with unknown stiffness and location.

According to some example embodiments, the data-driven generation of a position estimation model for collision detection, as described herein, may be used to enhance safety during teleoperation or autonomous control of CMs in proximity of sensitive organs in confined spaces. According to some example embodiments, the generation of such a position estimation model may solely rely on data from on-device sensors, independent of the CM kinematics model, without any prior assumption or knowledge regarding the geometry of the CM or its surrounding environment. In this regard, according to some example embodiments, generation of the position estimation model for collision detection, which may be referred to herein as a collision detection model although the use of such as position estimation model is not limited to use in the context of collision detection, may be conducted by defining the problem of collision detection as a classification problem, with sensory information as the input, and occurrence/no-occurrence of CM collision with the environment as the output classes. A machine learning model may be trained, for example pre-operatively, on the sensory data from the CM, and then a generated model may be used to detect collisions, e.g., intraoperatively, within an unknown environment. Feedback regarding the likelihood of a collision, based on the generated collision detection model, may be conveyed to the surgeon as audio or haptic feedback to safeguard against potential trauma and damage to sensitive organs.

According to some example embodiments, different sensors, such as electromagnetic tracking sensors, imaging sensors (e.g., intraoperative) or cameras may be used for sensing in CMs. However, according to some example embodiments, FBG optical sensors may be used. FBG optical sensors can offer advantages over other sensing approaches since such sensors need not require a direct line of sight, may have high streaming rate, e.g., 1 kilohertz (KHz), and may have minimal effects on compliance and compactness of the CM. FBG optical sensors may be used to sense and determine shape, force, and torsion of the CM. According to some example embodiments, an FBG optical sensor may serve as a dual-purpose simultaneous shape sensor and collision detector, which may preserve small size of the CM and avoid the need for additional sensors. Accordingly, as further described herein, some example embodiments are directed to a supervised machine learning approach for generating and utilizing a position estimation model for in CM collision detection with audio feedback to the user, without requiring additional sensors, a prior model of the CM, obstacle location, or environment properties.

While the techniques described herein are described as be applicable to CMs, and more generally, flexible manipulators of devices, it is contemplated that the training and collision detection may be applicable in a variety of applications, particularly, but not necessarily, in the medical context. For example, the techniques described herein may be implemented in association with the position estimation or collision detection of other medical instruments such as core biopsy needles, catheters, and other flexible medical instruments.

Figure 1:
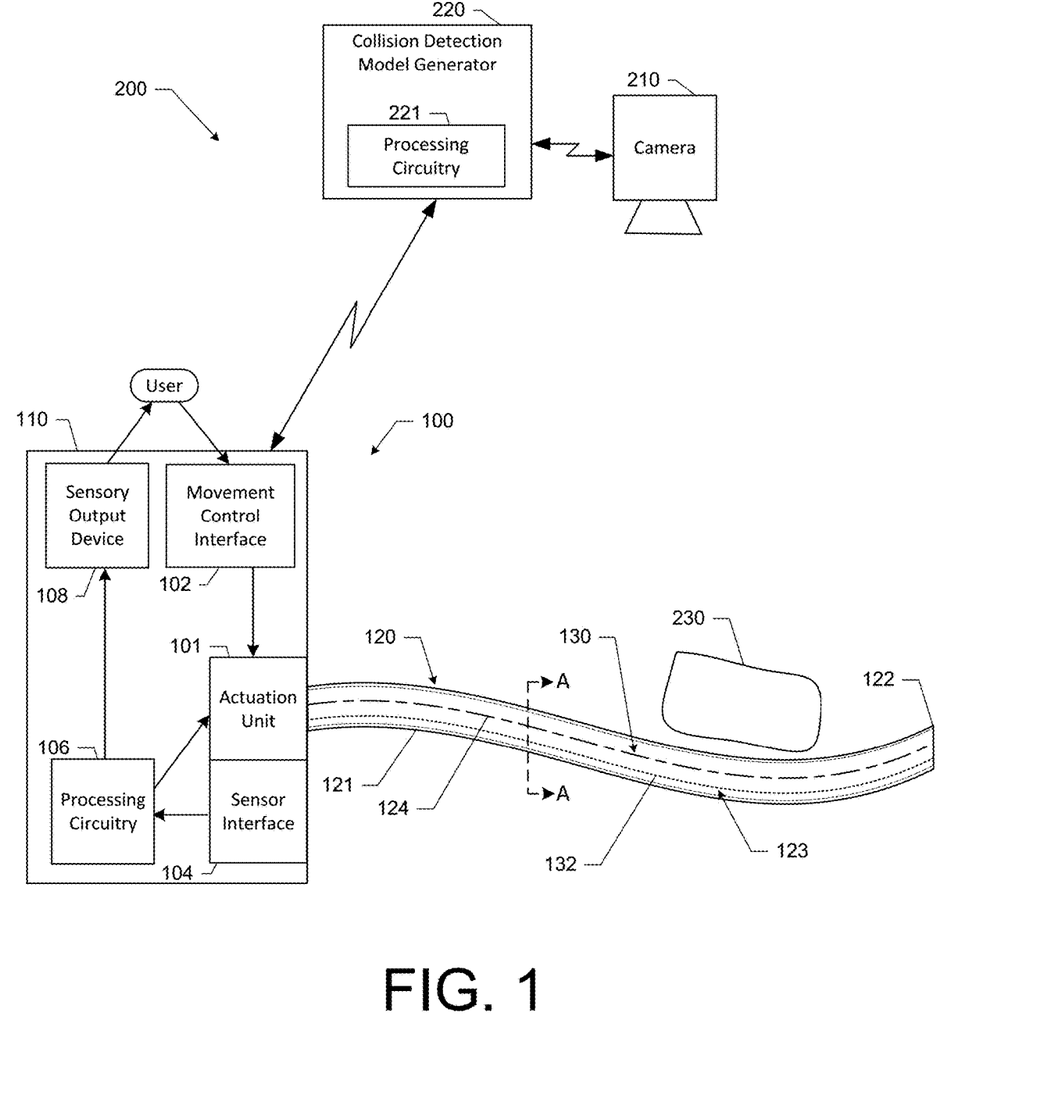
FIG. 1 illustrates a flexible manipulator system for training and collision detection via position estimation according to some example embodiments.

In view of the foregoing, FIG. 1 illustrates and example system for generating or utilizing a collision detection model according to some example embodiments. In this regard, the system 200 may comprise a flexible manipulator apparatus 100. The flexible manipulator apparatus 100 may, in turn, comprise a control unit 110 and a flexible manipulator 120. The flexible manipulator 120 may have a flexible elongate body 121 that may comprise a tip 122. The body 121 may be repositioned into different orientations along at least positions of the flexible manipulator 120's length to form curvatures. The flexible manipulator 120 may be a continuum manipulator (CM) or a continuum dexterous manipulator (CDM).

According to some example embodiments, a body 121 of the flexible manipulator 120 may be formed of a plastic substance or other flexible material or structure. According to some example embodiments, the body 121 may be may be formed of a "memory metal," such as nitinol (NiTi), that reverts back to an original position after being bent. The body 121 may include interleaved sections (or series of notches) that allow for bending and flexing of the body 121 while maintaining structural integrity. The body 121 may be formed as a tube that includes and internal channel 123 suitable for passing flexible instruments through the internal channel 123. According to some example embodiments, the external diameter of the body 121 may be about 6 millimeters and the internal diameter of the channel 125 may be about 4 millimeters.

The position and orientation of the body 121 of the flexible manipulator 120 may be controlled via cables 132, which may be stainless steel or any other flexible cables. According to some example embodiments, the cables (or at least a body of the cables, as further described below) may be formed of stainless steel wire rope or any other flexible cable and may be, for example, 0.5 mm in diameter. The cables 132 may be disposed in channels 125 within the body 121, where the channels 125 extend along an elongated length of the body 121. In this regard, the body 121 may include any number of channels 125, some of which may hold a cable 132. The cables 132 may be movement controlled at the base via the actuation unit 101, and the body 121 may also be affixed to the actuation unit 101. The operation of the actuation unit 101 is association with physical coupling with the body 121 and the cables 132 may control the mechanical movement aspects of the flexible manipulator 120. As such, through movement of the cables 132 responsive movement of the body 121 of the flexible manipulator 120 may be generated.

Additionally, the body 121 of the flexible manipulator 120 may include at least one sensor 130 (e.g., and optical sensor) which may be operably coupled to the sensor interface 104 of the control unit 110. In this regard, the sensor 130 may be a FBG sensor or other imaging sensor. However, according to some example embodiments, the sensor 130 may be an electromagnetic tracking sensor rather than an optical sensor. In this regard, while example embodiments described herein may refer to optical sensor data, it is understood that electromagnetic sensor data may alternatively be used.

The sensor 130 may be comprised of one or more sensor assemblies 124. Such sensor assembly 124 may be formed as an elongate strand and disposed in a respective channel 125 (FIG. 2) within the body 121, where, again, the channels 125 extend along an elongated length of the body 121. A sensor assembly 124 may be operably coupled to the sensor interface 104 to convert the signals generated by the sensor assembly 124 into signals that can be used an interpreted by the processing circuitry 106. According to some example embodiments, any number of sensor assemblies 124 may be disposed in respective channels 125 of the body 121. As further, described below, a sensor assembly 124 may itself include sensor channels 129 (FIG. 3) within which a sensory component (e.g., in the form of an optical fiber 127 with FBG nodes 128) may be disposed.

A sensor assembly 124 may be affixed at the tip 122 at a first end, as well as, at the base (e.g., control unit 110) at a second end of the flexible manipulator 120. In this regard, at the second end, the sensor assembly 124 may be coupled to a sensor interface 104 of the control unit 110.

Figure 2:
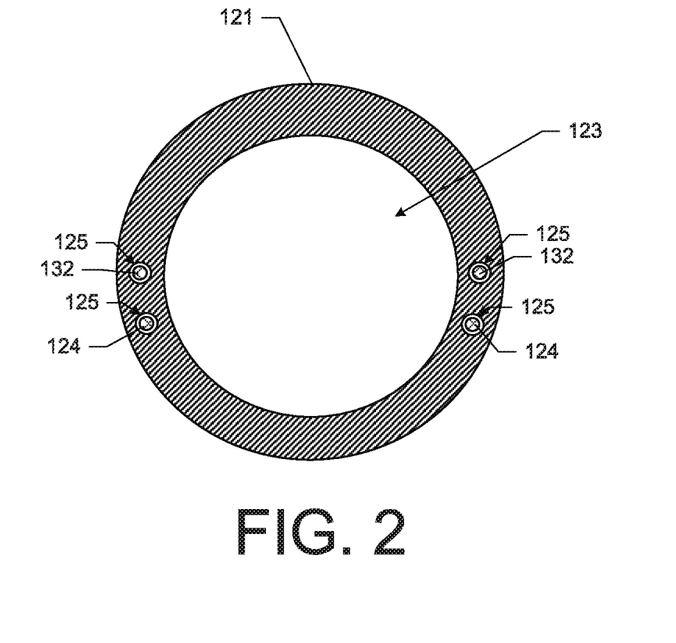
FIG. 2 illustrates a cross-section of a body of a flexible manipulator according to some example embodiments.

With reference to FIG. 2, a cross-section of the body 121 of the flexible manipulator 120 taken a line A-A of FIG. 1 is shown. In this regard, according to some example embodiments, the body 121 may have a circular cross-sectional shape. Further, the internal channel 123 (which may also be referred to as the instrument channel) of the body 121 may also have a circular cross-sectional shape. According to some example embodiments, the body 121 may include four channels 125, although, according to some example embodiments, any number of channels may be included. The channels 125 may extend along an elongate length of the body 121 in a linear manner, or, according to some example embodiments, the channels 125 may be disposed in non-linear channels.

As shown in FIG. 2, cables 132 may be disposed in two of the channels 125. Additionally, according to some example embodiments, a sensor assembly 124 may be disposed in each of two additional channels 125 of the body 121. Further, the sensor assemblies 124 may follow the path of the channels 125 through the body 121 as described above. Additionally, the sensor assemblies 124 may include sensor nodes that are also positioned in sensor assembly 124 and thus the path of the channels 125 through the body 121. According to some example embodiments, rather than the sensor assemblies 124 being disposed within a channel 125, the sensor assemblies 124 may be disposed external to the body 121 of the flexible manipulator 120 and affixed to the external surface of the body 121 along the elongate length of the flexible manipulator 120.

Figure 3:
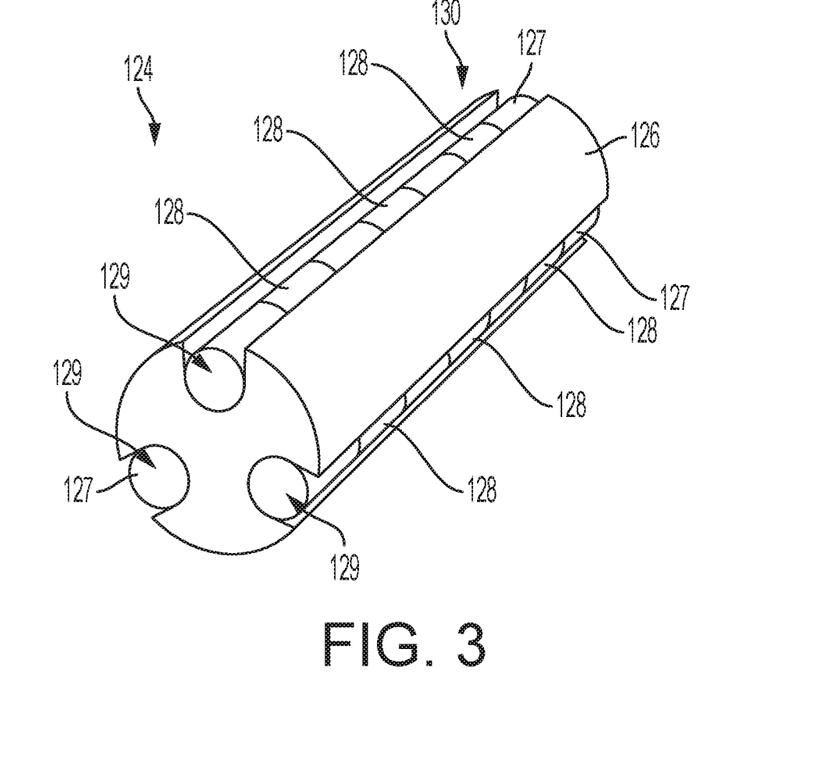
FIG. 3 illustrates a perspective view of a portion of a sensor assembly of a flexible manipulator according to some example embodiments.

With respect to example embodiments of the sensor assemblies 124, FIG. 3 illustrates a perspective view of a portion of a sensor assembly 124 according to some example embodiments. As shown in FIG. 3, the sensor assembly 124 may be comprised of a sensor support structure 126 (or sensor substrate) which may be formed as a nitinol substrate. Further, the sensor support structure 126 may include one or more sensor channels 129 disposed along an elongate length of the sensor support structure 126. The sensor channels 129 may be configured to receive (and hold) a sensory component of the sensor 130. According to some example embodiments, where the sensor 130 of the flexible manipulator 120 may comprise one or more FBG sensors. In this regard, the sensor 130, as an FBG sensor, may comprise an optical fiber 127 with FBG nodes 128 disposed along the optical fiber 127. Such FBG sensors may be relatively small in size and can provide data at high frequencies (e.g., 1 kHz) without requiring a direct line of sight (and are thus non-line-of-sight sensors). According to some example embodiments, the FBG sensors may be combined with a small elastic substrate to form standalone sensors and not affixed to the cables 132 or the FBG sensors may be attached directly to the cables 132 and may be disposed within a channel 125 together. The optical fiber 127 with the FBG nodes 128 may be disposed in each of the sensor channels 129. The sensor channels 129 may extend along an elongate length of the sensor support structure 126 in a linear manner as shown in FIG. 3, or, according to some example embodiments, the sensor channels 129 may be non-linear. For example, the sensor channels 129 may be formed in a helical path along the elongate length of the sensor support structure 126.

The FBG nodes 128 may be placed at any location along a length of the fiber 127. In operation, when the sensor assembly 124 bends, a strain is placed on the FBG nodes 128 near the bend. As such, backscattered light from the FBG nodes 128 that are under strain may have a different wavelength, and therefore the wavelength of the backscattered light may be analyzed to determine the degree of strain. When aggregated, the information provided by the backscattered light in the fiber 127 from the FBG nodes 128 (i.e., sensor data) can be used as a signature for an associated position or curvature of the sensor assembly 124, and thus the flexible manipulator 120 due to the positioning of the sensor assembly 124 in association with the body 121. Accordingly, when considered in association with information or sensor data from other sensors of other sensor assemblies 124, for example, within a body 121 of a flexible manipulator 120, a signature for a positioning of the body 121 of the flexible manipulator 120 may also be determined and used for modeling.

The sensor support structure 126 of the sensor assembly 124 of an FBG sensor may be comprised of a substrate material (e.g., nitinol), and may have a geometric characteristic described by a number of fibers. With respect to geometry, a triangular configuration—fibers 127 disposed 120 degrees apart (as shown in FIG. 3)—may be implemented. Alternatively, a helically wrapped geometry may be used, for example, with three FBG fibers for simultaneous curvature/torsion/force measurements. In this regard, according to some example embodiments, a helically wrapped sensor using only one fiber with multiple FBG nodes on the single fiber may be used.

Referring again to FIG. 1, the control unit 110 may be comprised of the actuation unit 101, a movement control interface 102, the sensor interface 104, processing circuitry 106, and a sensory output device 108. The actuation unit 101 may be configured to control the actuation and movement of the flexible manipulator 120. In this regard, the actuation unit 101 may include motors that are coupled to the cables 132. Via rotation of the motors (e.g., direct current (DC) motors), the cables 132 may cause the body 121 of the flexible manipulator 120 to move and bend into various desired positions. The motors may be controlled by a user via the movement control interface 102. In this regard, the movement control interface 102 may include a user interface control (e.g., a control pad, joystick, mouse, or the like) that is moveable by a user to send signals to the motors to cause movement of the cables 132.

The sensor interface 104 may be configured, in some example embodiments, to perform an optical to electrical conversion of received optical or other signals. In this regard, the sensor interface 104 may be configured to input light onto, for example, the fiber 127 and receive backscatter light from the fiber 127 that may be converted into electrical signals for delivery to the processing circuitry 106 for analysis. In this regard, as further described below, the processing circuitry 106 may be configured to analyze the sensor data represented by the electrical signal during a training process (e.g., preoperative) or during a collision detection process (e.g., intraoperative). Additionally, according to some example embodiments, during a collision detection process, the processing circuitry 106 may be configured to control the sensory output device 108 to provide a feedback to the user (e.g., surgeon) regarding collision detection. In this regard, for example, the sensory output device 108 may be a video device (e.g., a display), an audio device (e.g., a speaker), or a haptic feedback device (e.g., a controlled vibration device). According to some example embodiments where the sensory output device 108 is an audio device or a haptic feedback device, the processing circuitry 106 may be configured to control the sensory output device 108 to perform sonication based on a likelihood of a collision (e.g., a frequency or pitch of a tone output by the sensory output device 108 may be increased or decreased as a likelihood of a collision increases).

Having described the flexible manipulator apparatus 100, the other elements of the system 200 may now be described, with these elements being components implemented during a training process, which could be performed as a preoperative training process in some example embodiments. In this regard, the camera 210 may be a camera device configured to capture images and provide the images as image data for analysis. According to some example embodiments, the camera 210 may be a digital camera device, an optical tracker, or the like. The camera 210 may comprise one or a collection of cameras positioned to capture 2 dimensional or 3 dimensional views of the flexible manipulator 120. The camera 210 may be directed at the flexible manipulator 120 (e.g., in an overhead position) and may be configured to capture movements and positions of the flexible manipulator 120 relative to a training object 230, which may be placed in various locations during training to generate a collision detection model. The camera 210 may provide this image data to a collision detection model generator 220. The collision detection model generator 220 may include processing circuitry 221 configured to generate a collision detection model based on image data received from the camera 210 and sensor data from the sensor(s) of the flexible manipulator 120.

Having described the system 200, which may be implemented in the context of a training, and the flexible manipulator apparatus 100, which may be implemented in the context of a training process or in the context of a collision detection process, the methods and techniques for generating and utilizing a collision detection model will be described. In this regard, the collision detection model generator 220, and the processing circuitry of the collision detection model generator 220, may be configured to generate a collision detection model by implementing a training process as further described below.

Figure 4:
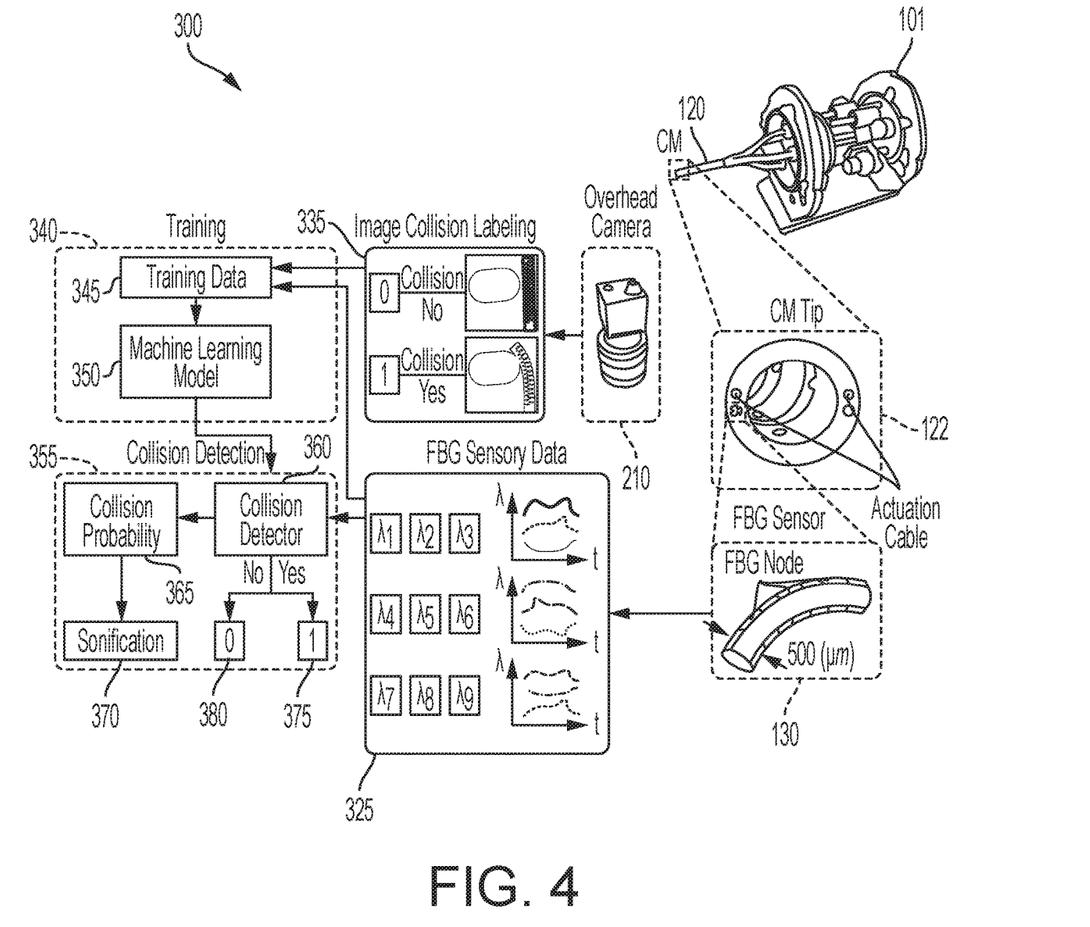
FIG. 4 illustrates flow diagram for training and collision detection via position estimation according to an example embodiment.

With reference to flow diagram of FIG. 4, the training process 340 is described and may involve receipt of image data sets from the camera 210 of iterations of movements of the flexible manipulator 120, which includes the tip 122 and the sensor 130. The image data sets may be provided to the collision detection model generator 220 to classify the image data sets under image collision labeling 335. The classified image data sets may then be treated as training data 345. Additionally, during the iteration movements of the flexible manipulator 120, the sensor data 325 (or FBG sensory data) may be captured from the sensor 130 and also provided as training data 345. The training data 345 may be synthesized and transformed into a machine learning model 350 as further described below, which can be used for collision detection as a collision detection model.

Further, with respect to the collision detection process 355, which may be implemented by the processing circuitry 106 of the flexible manipulator apparatus 100, the sensor data 325 may be received and applied to the collision detection model by the collision detector 360. The collision detector 360 may provide outputs in the form of binary outputs (i.e., yes/collision at 375 or no/no collision at 380). The collision detector 360 may be employed to perform collision probability at 365 and apply the collision detection model in a probabilistic manner to predict a likelihood of a collision in the form of a collision likelihood score (i.e., an analog or non-binary output) based on the sensor data being received, for example, over a given duration of time. Based on the collision likelihood score, sonification at 370 may be performed via the sensory output device 108.

In this regard, providing additional detail with respect to the generation of a collision detection model, the problem of collision detection may be analyzed, according to some example embodiments, as a supervised classification problem with two classes: collision, and no collision. Further, according to some example embodiments the classes may be expanded to include classes directed to type, such as stiffness properties and regions of collision. In this regard, once a model is generated, the input may be the sensor data obtained from the sensor 130 (e.g., fibers 127 with FBG nodes 128) and an output may be the corresponding class of collision. To generate the model, the collision detection model generator 220 may be configured to create of an offline dataset, where the sensor data, indicating a position of the flexible manipulator, may be labeled with a collision class based on interaction between the flexible manipulator 120 and the training object 230. A supervised machine learning model 350 may be trained on the collected datasets to learn the nonlinear mapping from the sensor data 325 to the appropriate class of collision. The trained model may be further optimized by tuning the hyperparameters via a k-fold cross validation by splitting the training data to training and validation sets. Performance of the tuned model may then be evaluated on unseen test data from flexible manipulator collisions with obstacles with different stiffness and properties (hard and soft), placed at random unknown locations relative to the flexible manipulator 120.

Additionally, according to some example embodiments, any number of classes may be defined for use in development of trained collision detection model. For example, classes may be defined for collision or no collision of each lengthwise segment of the flexible manipulator 120. Segments of the manipulator may be defined as equal length portions form the base to the tip or segments may be defined based on positions and lengths defined along the length of the flexible manipulator 120. As such, classes may be defined by the location or region of contact based upon the segment that could be determined to make contact. For example, different classes collision/no collision classes could be defined for the segments of the flexible manipulator such as the base, the center, and the tip. As such, the classes could distinguish between the particular segment or segments that can come in contact with the object by providing the likelihood that each segment may be contact with objects.

To create an appropriate training dataset, a vision-based algorithm based on a connected components labeling algorithm may be used to segment training images captured via an overhead camera 210 looking at the flexible manipulator 120 and the surrounding obstacles (e.g., training object 230). Data (i.e., sensor data and image data) may be captured for a number of movement iterations and varied positions of the training object 230 and synthesized for machine learning. According to some example embodiments, the image data sets may first be converted to a binary format by applying appropriate thresholds (contrast or color thresholds). Further, according to some example embodiments, an erosion morphological operation, followed with a dilation, both with small kernel sizes, may be applied to the binary image data to remove potential background noise and ensure robust connected region detection. The connected components labeling algorithm may then segment the binary image data to distinguish between the background, the flexible manipulator 120, and obstacles present in the scene. Particular image date and time-associated sensor data may be labeled with the collision class, if the flexible manipulator 120 and the obstacle form a connected region (i.e., a collision) in the corresponding image frame.

Figure 5:
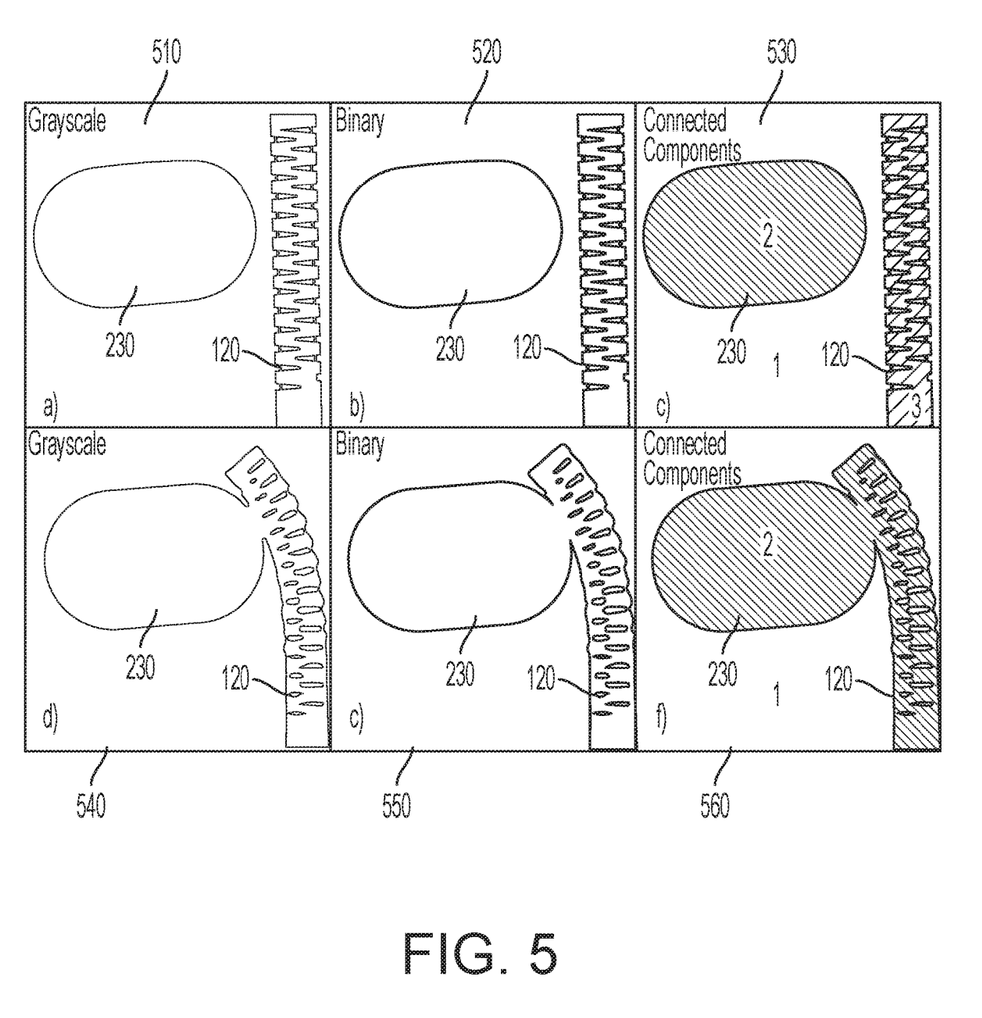
FIG. 5 illustrates a collection of image views that may be used for classifying a collision event and a no collision event according to some example embodiments.

In this regard, FIG. 5 illustrates a collection of image views that may be used for classifying a collision and a no collision, according to some example embodiments. In this regard, the image views of FIG. 5 indicate the segmented regions in collision and no collision instances during the training phase. An example "no collision" image data analysis is shown for a movement iteration in images 510, 520, and 530. In this regard, the initial grayscale image 510 of the flexible manipulator 120 and the training object 230 is converted into the binary image 520. The binary image 520 may then be analyzed to identify the background "1", the training object "2", and the flexible manipulator "3". Since there is no region of connectivity or continuity between the training object "2" and the flexible manipulator "3", the image may be classified as a no collision image.

An example "collision" image data analysis is shown for a movement iteration in images 540, 550, and 560. In this regard, the initial grayscale image 540 of the flexible manipulator 120 and the training object 230 is converted into the binary image 550. The binary image 550 may then be analyzed to identify the background "1" the training object "2", and the flexible manipulator also "2". Since there is connectivity or continuity between the training object and the flexible manipulator (both identified as region "2" in the image), the image may be classified as a collision image.

The images and classifications may be incorporated into a data-driven approach to directly generate a collision detection model for flexible manipulator 120 based on empirical data captured during the training process. According to some example embodiments, because the collision detection problem may be addressed as a machine learning classification problem, a gradient boosting classifier may be implemented to learn and build the collision detection model. In this regard, gradient boosting may be used as a powerful machine learning technique for classification and regression problems. Gradient boosting may be implemented to build a model in a sequential way and combines an ensemble of relatively weak simple models (base learners). In this regard, let $\{x_k\}_{k=1}^N$ be a sequence of observations (image data sets), where $x_k \in \mathbb{R}^n$ (n is the number of the optical sensor data at frame k) represents the observation at frame k. Let $y_k$ be the corresponding labels (1=collision, 0=no collision). Given the training data, a gradient boosting classifier may be trained to detect a collision. The classifier scores may be used as a probability of predicting collisions based on a statistical analysis.

When generating the collision detection model, a number of parameters may also be considered and optimized. In this regard, for the machine learning on the training data, parameters such as learning rate, subsampling, number of max features, max depth, and boosting iterations (number of estimators) may be used. Further, regularization techniques, such as shrinkage, may be applied. According to some example embodiments, shrinkage may be applied to training data in combination with gradient boosting. Further, for example, parameters such as shrinkage (learning rate<1), stochastic gradient boosting (subsample<1), and variation on maximum number of features (using all or log 2 of the features) may be applied to the machine learning. Further, according to some example embodiments, a validation process may be performed using k-fold cross validation on at least a portion of the training data. Additionally, according to some example embodiments, boosting trees, neural networks, deep neural networks, ensembles, and the like, may be used, according to some example embodiments, to perform sensing of contacts (collisions), shape, tip position, and force using, for example, only sensor data as described herein.

Additionally, according to some example embodiments, the training data may be analyzed to perform tip position estimation, which may also be used for shape sensing and contact force sensing in the context of collision detection. In this regard, according to some example embodiments, the position of the tip 122 may be estimated based on the determined curvature in the flexible manipulator 120 as indicated by the sensor data. Again, a data-driven or empirical approach may be used to estimate the tip location. To do so, according to some example embodiments, a regression model may be used, as a component of or integrated into the collision detection model, that uses the sensor data (possibly in the form of FBG wavelength raw data) as an input and directly estimates tip position of the flexible manipulator 120. Again, the collision detection model may be pre-operatively (off-line) trained on position information from cameras (e.g., camera 210) as the ground truth, and then the collision detection model, with the tip estimation contribution, may be applied intra-operatively (on-line) to detect possible collisions based on estimates of the flexible manipulator tip. According to some example embodiments, the estimation of the tip position may be performed using, for example, only the sensor data (e.g., FBG wavelength data). Such an approach may be beneficial particularly when the flexible manipulator 120 is subjected to large deflection bendings.

Similar to the techniques described above and as shown and described with respect to FIG. 4, tip position estimation may also be performed, using a tip position estimation model, without relying upon on assumptions regarding the geometrical relations of the manufactured sensor and is therefore expected to reduce the error in tip position estimation, especially when flexible manipulator 120 undergoes large deflections. In addition, according to some example embodiments, a data-driven, empirical approach does not require any geometrical or structural assumptions regarding the sensor design, the number of FBG nodes at each cross section of the flexible manipulator 120, but rather uses the correlation and aggregation of, for example, all FBG nodes of the sensor along the elongate length of the flexible manipulator 120 simultaneously to estimate the tip position. As the flexible manipulator 120 bends, the sensor data in the form of raw FBG wavelength data changes due to strain changes at the FBG nodes as described above.

For tip position estimation, as well as flexible manipulator 120 shape estimation, a tip position estimation model (e.g., the collision detection model) may be trained on sensor data, such as FBG raw wavelength data as an input, and a true flexible manipulator tip position (or shape) may be collected from another sensor (e.g., camera 210) to synthesize the data into a relational model and classification. The model may be generated during the training process and then leveraged to estimate the shape of the flexible manipulator 120 (i.e., describing bends or curves in the flexible manipulator 120) and the tip position intra-operatively using only the sensor data, in the form of, for example, the FBG raw wavelength data as an input.

For training, according to some example embodiments, a two-step procedure may be used to locate the tip position of the flexible manipulator 120 relative to the flexible manipulator 120's base using the camera 210, for example, in the form of an optical tracker, defining an optical tracker frame o. A coordinate frame may also be established at the tip 122, defined as frame s, when the tip 122 is straight with respect to a reference body that is attached to the fixed actuation unit 101, defining frame r, using, for example, a rigid body placed into the open lumen (e.g., internal channel 123) of the flexible manipulator 120:

$$T_{sr}^0 = (T_{os}^0)^{-1} T_{or}^0$$

where $T_{ij}^0$ denotes frame j with respect to frame i during the one-time coordinate frame establishment ay time 0. According to some example embodiments, using the transformation between frames s and r, all the information may be reported with respect to the reference body, independent of where the optical tracker is located.

For tip tracking during bending of the flexible manipulator 120, for example, a single spherical marker attached to a post may be placed into the internal channel 123 of the flexible manipulator 120. The tracked position of the spherical marker with respect to the optical tracker coordinate ($P_o$) frame can be represented with respect to the base of the flexible manipulator 120, defined as frame b, by:

$$P_b = T_{bs} T_{sr}^0 (T_{or}^c)^{-1} P_o$$

where $T_{or}^c$ is the reference body coordinate frame with respect to the optical tracker coordinate frame at the flexible manipulator 120's current location (in case the location of optical tracker changes). $T_{bs}$ brings the tip position in frame s to the flexible manipulator 120 base frame ($P_b$):

$$T_{bs} = \left[ \begin{array}{c|c} I_{3\times 3} & P_{bs} \\ \hline 0_{1\times 3} & 1 \end{array} \right]$$

where $P_{bs} = [0, 0, L_{CDM}]^T$ and $L_{CDM}$ is the length of the flexible manipulator 120. From the tracked position of the spherical marker with respect to the optical tracker coordinate ($P_o$) frame, the tip positions may be known with respect to the coordinate frame at the base of the flexible manipulator 120 (frame b).

Based on the foregoing, a regression model may be used for generating the tip position estimation model (e.g., the collision detection model), since given some independent variables as input, prediction of a dependent variable is desired. As such, a regression model may be used that can predict the flexible manipulator 120's three-dimensional tip position (dependent variables) given a set of optical sensor data, for example in the form of raw FBG wavelength data along the sensor 130 (independent variables):

$$p=\Psi(\lambda,\beta)$$

where $p \in \mathbb{R}^3$ is the three-dimensional position of the tip 122, $\lambda \in \mathbb{R}^m$ is the vector containing the raw wavelength data of the m FBG nodes on the sensor, $\beta$ is the vector of unknown parameters, and $\Psi: \mathbb{R}^m \to \mathbb{R}^3$ is the regression model that predicts the three-dimensional tip position, given the wavelength information of the complete set of FBG nodes on the sensor 130 at any given time. According to some example embodiments, depending on the degrees of freedom of the flexible manipulator 120, complexity of the environment, and the shapes that the flexible manipulator 120 can obtain, different regression models such as boosting trees, neural networks, deep neural networks, ensembles, and the like, may be used to capture the unknown parameters $\beta$.

For example, a linear regression may be used that models the dependent variables as a linear combination of the unknown parameters. Accordingly, the tip position sensing may be modeled as a least squares optimization problem:

$$\operatorname*{argmax}_{B}\sum_{n=1}^{N}r_n^2 = \operatorname*{argmin}_{B}\|\Lambda B - P\|_2^2$$

where $r_n$ is the residual of the error for the $n^{th}$ observation, $\Lambda \in \mathbb{R}^{N \times m}$ is a stack of N observations of the m FBG node data, $P \in \mathbb{R}^{N \times 3}$ is the stack of N true tip position observation data (and N movement iterations of the flexible manipulator 120) from camera 210, and $B \in \mathbb{R}^{m \times 3}$ is the matrix of unknown parameters. Using the least squares optimization indicated above, the regression model may be trained pre-operatively on N observations (movement iterations) of the FBG sensor data and the true tip position (from the camera 210) to find the unknown parameters $\beta$ using the generalized inverse:

$$B=(\Lambda^T \Lambda)^{-1} \Lambda^T P.$$

The trained model may then be used intra-operatively as the collision detection model to predict the tip position values given only the current sensor data, in the form of FBG wavelength data:

$$\hat{p}=B^T \lambda$$

where $\hat{p} \in \mathbb{R}^3$ is the predicted tip position, given the current wavelength data for all FBG nodes on the sensor ($\lambda \in \mathbb{R}^m$).

Using the regression model as provided above, the uncertainties regarding the shape sensor manufacturing such as FBG node locations can be captured in the unknown parameters matrix B. In addition, the wavelength information of all FBG nodes (and not just the ones at a certain cross section) on the sensor may be utilized for tip position prediction. Further, according to some example embodiments, the regression model does not suffer from the accumulated errors that occur during integration of position over the length of the flexible manipulator 120 as provided in conventional methods, since the tip position is predicted directly. Moreover, according to some example embodiments, the regression model to be used as the position estimation model or collision detection model can be trained separately on the data from fewer than three (or lesser) FBG fibers, to allow for the option of predicting the tip position in case of fiber failure in an intra-operative context by switching to use of the separately trained model if a fiber failure is detected.

Figure 6A:
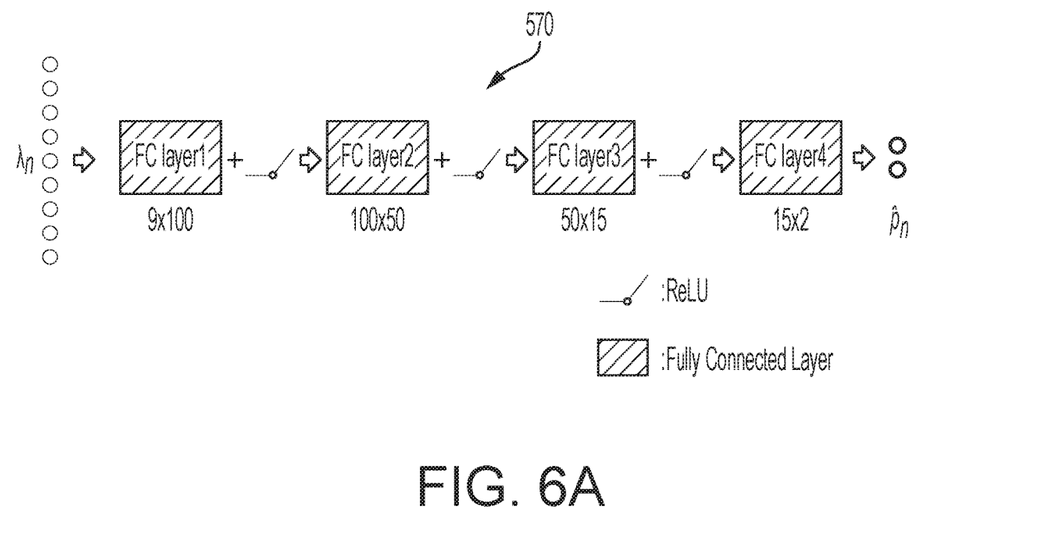
FIG. 6A illustrates an example architecture design of a deep neural network according to some example embodiments.

Alternatively, according to some example embodiments, a deep neural network (DNN) approach may be implemented to capture the unknown parameters. The DNN approach, according to some example embodiments, may offer increased flexibility to fit complex models compared to other, traditional regression methods. Unknown parameters in the DNN model may be trained end-to-end in a data-driven manner through backpropagation. In this regard, the trainable parameters in the DNN may be defined as $W = \{W^{(i)}\}_{i=1}^{L}$ for $W^{(i)} \in \mathbb{R}^{F_i \times F_{i-1}}$ with a corresponding bias vector $b^{(i)} \in \mathbb{R}^{F_i}$, where i is the layer index and $F_i$ is the layer size hyperparameter. For sensor data in the form of a normalized raw FBG wavelength data vector at the $n^{th}$ observation, $\hat{\lambda}_n \in \mathbb{R}^m$, activations may be computed as $E=\{E_n^{(i)}\}_{i=1}^{L}$ for $E^{(i)} \in \mathbb{R}^{F_i}$ with:

$$E_n^{(1)}=f(W^{(1)} \cdot \hat{\lambda}_n + b^{(1)}).$$

$$E_n^{(l)}=f(W^{(l)} \cdot E_n^{(l-1)} + b^{(l)}),$$

where f(•) is the Rectified Linear Unit (ReLU) non-linear activation function, $l \in \{2, \ldots, L\}$ are the second to the last layer of the network and $F_0=m$. The DNN output may be the corresponding $n^{th}$ flexible manipulator tip position $\hat{p}_n \in \mathbb{R}^2$. A Mean Squared Error (MSE) may be used as a loss function to optimize $\|\hat{p}_n - p_n\|_2^2$, where $p_n \in \mathbb{R}^2$ is the ground truth tip position observation. FIG. 6A illustrates an example architecture design 570 of the DNN as described. In this regard, $\lambda_n$ may be the raw FBG wavelength data vector at the $n^{th}$ observation. $\hat{p}_n$ may be the network output flexible manipulator tip position with the hyperparameters of the fully connected layers being listed under each block in the architecture design 570.

Alternatively, according to some example embodiments, a temporal neural network (TNN) approach may be implemented to capture the unknown parameters. In this regard, the aforementioned models may be trained, according to some example embodiments, only with individual sensor observations at a particular time step, without consideration of the time-series information. Temporal Convolutional Networks (TCN) may improve video-based analysis models and make use of time-varying features to make predictions. Utilizing a time-series model may be beneficial because input data features may change continuously, and manipulation and deformation of the flexible manipulator 120 may also occur in a continuous manner. As such, inconsideration of the design of TCNs, a TNN approach may be implemented for estimating the tip position of the flexible manipulator 120.

Figure 6B:
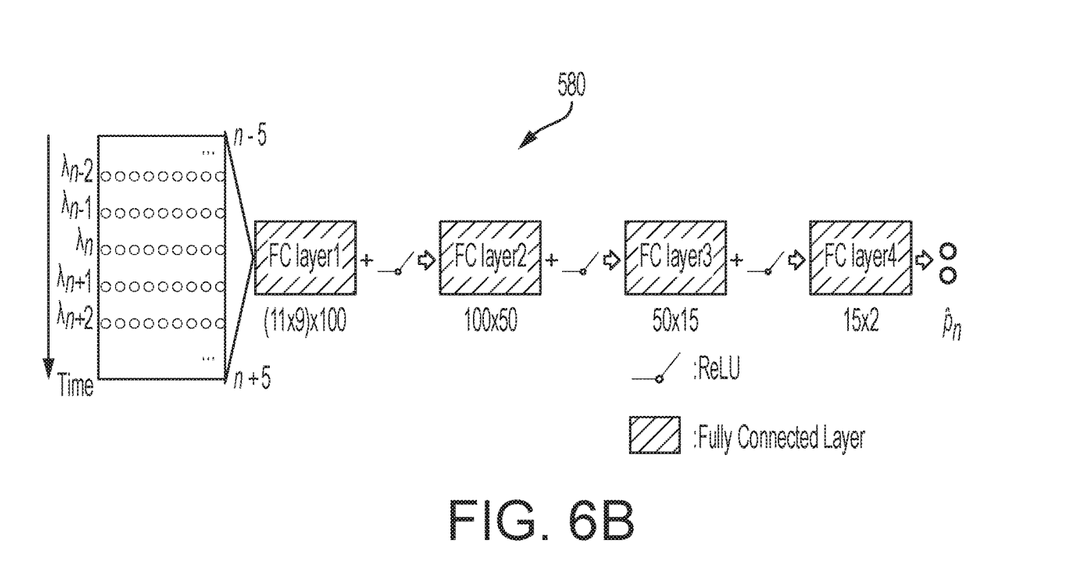
FIG. 6B illustrates an example hierarchical structure of a temporal neural network according to some example embodiments.

In this regard, FIG. 6B illustrates a hierarchical structure 580 of a TNN, according to some example embodiments, with the concatenation process shown with the time-series data. Using the above notations, the input concatenated feature with respect to time may be denoted as:

$$\hat{\lambda}_{cat,n,k} = [\hat{\lambda}_{n-k}, \ldots, \hat{\lambda}_{n-1}, \hat{\lambda}_n, \hat{\lambda}_{n+1}, \ldots, \hat{\lambda}_{n+k}] \in \mathbb{R}^{m \times (2k+1)},$$

where (2k+1) is the number of samples covered in this concatenated feature. The TNN may be trained to predict the estimated tip position corresponding to the middle data sample $\hat{p}_n$. While embedding the time-series may introduce a small delay (milliseconds) in predictions, information about changes in the sensor data may be incorporated as a result of potential contacts with the environment or stopping the flexible manipulator 120 actuation. For the TNN, the same Mean Squared Error loss used in the DNN approach may be used.

Regardless of whether a linear regression, deep neural network, or temporal neural network approach is used, once an accurate estimate of the tip position of the flexible manipulator 120 can be generated based on the regression model, a shape of the flexible manipulator 120 can be reconstructed. In this regard, the flexible manipulator 120 may be modeled as a series of rigid links connected by passive elastic joints using a pseudo-rigid body model. For example, the flexible manipulator 120 may be modeled as an n-revolute-joint mechanism for a flexible manipulator 120 that is configured for planar motion. Further, depending on the design of the particular flexible manipulator 120, spherical joints may be assumed in a general case. As such, at any given instance, the tip position estimation ($\hat{p}$) output from the regression model may be passed as an input to a constrained optimization as follows to solve for the joint angles, and consequently, the shape may be reconstructed:

$$\underset{\Theta_c}{\text{minimize}} \|\hat{p} - f(\Theta_c)\|$$

$$\text{subject to } \Theta_c \leq \Theta_{max}$$

$$f_x = d \cdot \left( \sum_{i=1}^{n} \sin\left( \sum_{j=1}^{i} \Theta_j \right) \right)$$

$$f_y = d \cdot \left( \sum_{i=1}^{n} \cos\left( \sum_{j=1}^{i} \Theta_j \right) \right)$$

where $\Theta_c \in \mathbb{R}^n$ may be the flexible manipulator 120 joint angles from the pseudo-rigid body model, $d = L_c/n$ is the distance between two consecutive joints, $f(\Theta_c)$: $\Theta_c \rightarrow \mathbb{R}^2$ is the flexible manipulator 120 forward kinematics mapping from joint space to task space, and $\Theta_{max}$ is the maximum angle each joint may take, which can be determined experimentally. A trade-off may exist between using a more complex pseudo-rigid body model (large number for n) and the computational complexity of the constrained optimization above. Additionally, with respect to outputs provided to the user (e.g., via the sensory output device) during a collision detection process, visual feedback may be used and is common means of conveying information to, for example, the surgeon during surgery. However, augmentation of this feedback method with many sources of information may be prone to the risk of missing crucial information in the visual context. Particularly, during teleoperation and control of the flexible manipulator 120 in confined spaces, the visual feedback may be compromised by occlusion or miss-interpretation due to cluttered background, which may increase the risk of damaging sensitive organs or tissues. As an alternative, information may be conveyed to the surgeon (user) associated with the collision detection via sonification of the probability of predicting collision (classifier or collision likelihood score).

Having described the various features and techniques associated with generating and utilizing a collision detection model, specific configurations of the processing circuitry 106 of the control unit 110 and the processing circuitry 221 of the collision detection model generator 220 can be described, referring again to FIG. 1. Processing circuitry 106, 221 may comprise a processor, and a memory, in addition to other passive and active components for performing the functionalities described herein. Further, according to some example embodiments, processing circuitry 106, 221 may be in operative communication with or embody, the memory, the processor, and possibly a user interface, and a communications interface. Through configuration and operation, the processing circuitry 106, 221 may be configurable to perform various operations as described herein, including the operations and functionalities described with respect to the functionality of the flexible manipulator apparatus 100 or the collision detection model generator 220. In this regard, the processing circuitry 106, 221 may be configured to perform computational processing, memory management, user interface control, and monitoring, and manage remote communications, according to an example embodiment. In some embodiments, the processing circuitry 106, 221 may be embodied as a chip or chip set. In other words, the processing circuitry 106, 221 may comprise one or more physical packages (e.g., chips) including materials, components or wires on a structural assembly (e.g., a baseboard). The processing circuitry 106, 221 may be configured to receive inputs (e.g., via peripheral components), perform actions based on the inputs, and generate outputs (e.g., for provision to peripheral components). In an example embodiment, the processing circuitry 106, 221 may include one or more instances of a processor, associated circuitry, and memory. As such, the processing circuitry 106, 221 may be embodied as a circuit chip (e.g., an integrated circuit chip, such as a field programmable gate array (FPGA)) configured (e.g., with hardware, software or a combination of hardware and software) to perform operations described herein.

In an example embodiment, the memory may include one or more non-transitory memory devices such as, for example, volatile or non-volatile memory that may be either fixed or removable. The memory may be configured to store information, data, applications, instructions or the like for enabling, for example, the functionalities described with respect to the flexible manipulator apparatus 100 or the collision detection model generator 220. The memory may operate to buffer instructions and data during operation of the processing circuitry 106, 221 to support higher-level functionalities, and may also be configured to store instructions for execution by the processing circuitry 106, 221. According to some example embodiments, various data stored in the memory may be generated based on other data and stored or the data may be retrieved via a communications interface linked to another entity and stored in the memory.

As mentioned above, the processing circuitry 106, 221 may be embodied in a number of different ways. For example, the processing circuitry 106, 221 may be embodied as various processing means such as one or more processors that may be in the form of a microprocessor or other processing element, a coprocessor, a controller or various other computing or processing devices including integrated circuits such as, for example, an ASIC (application specific integrated circuit), an FPGA, or the like. In an example embodiment, the processing circuitry may be configured to execute instructions stored in the memory or otherwise accessible to the processing circuitry 106, 221. As such, whether configured by hardware or by a combination of hardware and software, the processing circuitry 106, 221 may represent an entity (e.g., physically embodied in circuitry—in the form of processing circuitry 106, 221) capable of performing operations according to example embodiments while configured accordingly. Thus, for example, when the processing circuitry 106,221 is embodied as an ASIC, FPGA, or the like, the processing circuitry 106, 221 may be specifically configured hardware for conducting the operations described herein. Alternatively, as another example, when the processing circuitry 106, 221 is embodied as an executor of software instructions, the instructions may specifically configure the processing circuitry 106, 221 to perform the operations described herein.

With respect to the configuration of the processing circuitry 221 of the collision detection model generator 220, in general, the processing circuitry 221 may be configured to perform a training process to generate a collision detection model for use in later collision detection. In this regard, the processing circuitry 221 may be communication with the camera 210 and the flexible manipulator apparatus 100. As described above, the flexible manipulator apparatus 100 may comprise a flexible manipulator 120 that may be elongate and may comprise a sensor (e.g., sensor 130). In this regard, the sensor may be an FBG sensor. Further, according to some example embodiments, the sensor may comprise three sensor nodes, where each of the three sensor nodes is located on a different, respective cross-sectional plane of the flexible manipulator 120, and each sensor node is configured to collect node-level sensor data for inclusion in the sensor data sets. According to some example embodiments, the sensor may be configured to provide raw sensor data that includes wavelength information. The flexible manipulator 120 may be movable to form a curve in the flexible manipulator 120. The flexible manipulator 120 may be a continuum manipulator controlled via movement of cables 132. The flexible manipulator apparatus 100 may also include a user output device (e.g., sensory output device 108), which may be configured to provide sensory outputs to a user. The camera 210 may be configured to capture movement of the flexible manipulator 120 relative to a test collision object (e.g., training object 230).

Accordingly, the processing circuitry 221 may be configured to control the flexible manipulator 120, via the processing circuitry 106, cause iterations of movement of the flexible manipulator 120 relative to the test collision object with at least one iteration of movement involving a collision between the flexible manipulator 120 and the test collision object. The processing circuitry 221 may be further configured to receive sensor data sets (e.g., from the sensor 130) associated with the iterations of movement of the flexible manipulator 120 (e.g., associated in time). The processing circuitry 221 may also be configured to receive image data sets, from the camera 210, associated with the iterations of movement of the flexible manipulator 120.

Having received the sensor data sets and the image data sets, the processing circuitry 221 may be configured to synthesize the sensor data sets with the image data sets to classify the iterations of movement into a collision class and a no collision class. Further, the processing circuitry 221 may be configured to generate a collision detection model for use with the flexible manipulator 120 in future procedures based on the synthesized data sets and the classifications of the iterations of movement. In this regard, as described above, the collision detection model may be generated based on machine learning and/or a regression model. According to some example embodiments, the processing circuitry 221 may be configured to generate the collision detection model through implementation of a gradient boosting classifier. Further, according to some example embodiments, the processing circuitry 221 may be configured to generate the collision detection model via k-fold cross validation on the synthesized data sets.

The processing circuitry 106 may be generally configured to detection potential collisions of the flexible manipulator 120 during a collision detection procedure. In the regard, the processing circuitry 106 may be configured to receive captured sensor data from the sensor (e.g., sensor 130) during movement of the flexible manipulator. The processing circuitry 106 may also be configured to determine a collision likelihood score based on application of the captured sensor data to a collision detection model (e.g., generated by the collision detection model generator 220). In this regard, the collision detection model may be based on an empirical data (or data-driven) training for the flexible manipulator 120 comprising training sensor data from the sensor and training image data of positions of the flexible manipulator 120. The processing circuitry 106 may also be configured to control the user output device (e.g., sensory output device 108) based on the collision likelihood score to provide a collision alert sensory output to the user. In this regard, according to some example embodiments, the processing circuitry 106 may be configured to control the user output device to provide a real-time sonication output to the user based on the collision likelihood score. Further, according to some example embodiments, the processing circuitry 106 may be configured to determine the collision likelihood score based on application of the captured sensor data to the collision detection model, where the captured sensor data is the only input to be applied to the collision detection model to determine the collision likelihood score and/or the captured sensor data is raw sensory data received from the sensor. Further, according to some example embodiments, the processing circuitry 106 may be configured to determine an estimation of a position of the tip by determining a curvature of the flexible manipulator based on the captured sensor data.

Figure 7:
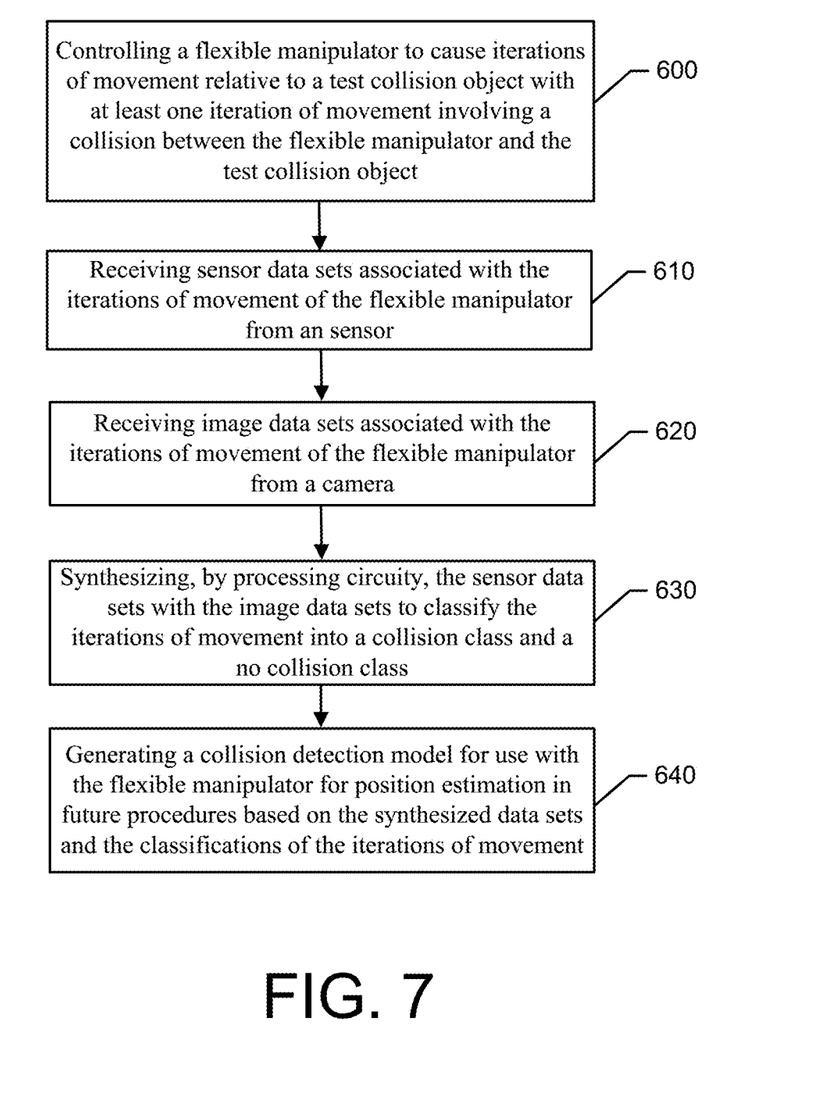
FIG. 7 illustrates a block diagram of an example method for generating a collision detection model for position estimation of a flexible manipulator apparatus according to some example embodiments.

Now referring to FIG. 7, an example method for generating a collision detection model for a flexible manipulator apparatus (e.g., flexible manipulator apparatus 100) is provided. In this regard, the example method may comprise, at 600, controlling a flexible manipulator to cause iterations of movement relative to a test collision object with at least one iteration of movement involving a collision between the flexible manipulator and the test collision object. The example method may also comprise, at 610, receiving sensor data sets associated with the iterations of movement of the flexible manipulator from a sensor. In this regard, the flexible manipulator may comprise the sensor. Further, the example method may also comprise, at 620, receiving image data sets associated with the iterations of movement of the flexible manipulator from a camera. In this regard, the camera may be remote from the flexible manipulator. Further, the example method, at 630, may include synthesizing, by processing circuitry, the sensor data sets with the image data sets to classify the iterations of movement into a collision class and a no collision class, and, at 640, generating a collision detection model for use with the flexible manipulator in future procedures based on the synthesized data sets and the classifications of the iterations of movement.

According to some example embodiments, generating the collision detection model may include generating the collision detection model through implementation of a gradient boosting classifier. Further, according to some example embodiments, the sensor may include an FBG sensor. Further, according to some example embodiments, generating the collision detection model may include generating the collision detection model via k-fold cross validation on the synthesized data sets. Additionally, according to some example embodiments, the sensor may comprise three sensor nodes. Each of the three sensor nodes may be located on a different, respective cross-sectional plane of the flexible manipulator. Further, each sensor node may be configured to collect node-level sensor data for inclusion in the sensor data sets.

Figure 8:
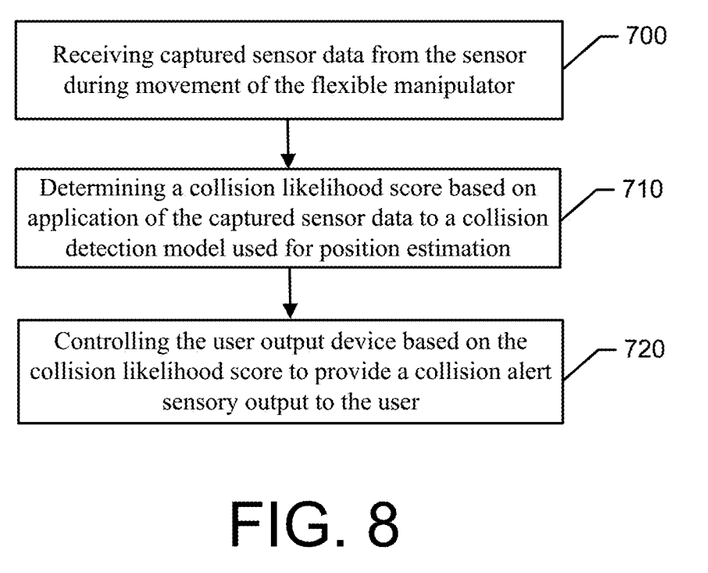
FIG. 8 illustrates a block diagram of an example method for determining a likelihood of a collision by a flexible manipulator apparatus using position estimation according to some example embodiments.

Now referring to FIG. 8, an example method for determining a likelihood of a collision by a flexible manipulator apparatus (e.g., flexible manipulator apparatus 100) is provided. In this regard, the example method may include, at 700, receiving captured sensor data from the sensor during movement of the flexible manipulator. Further, at 710, the example method may include determining a collision likelihood score based on application of the captured sensor data to a collision detection model. In this regard, the collision detection model may be based on an empirical data training for the flexible manipulator comprising training sensor data from the sensor and training image data of positions of the flexible manipulator. Additionally, the example method may comprise controlling the user output device based on the collision likelihood score to provide a collision alert sensory output to the user.

According to some example embodiments, controlling the user output device may include controlling the user output device to provide a real-time sonication output to the user based on the collision likelihood score. According to some example embodiments, the flexible manipulator may comprise a continuum manipulator controlled via movement of cables, and/or the sensor may include an FBG sensor. Further, according to some example embodiments, receiving the captured sensor data may include receiving the captured sensor data as raw sensor data that includes wavelength information. According to some example embodiments, determining the collision likelihood score may include determining the collision likelihood score based on application of the captured sensor data to the collision detection model. In this regard, the captured sensor data may be the only input to be applied to the collision detection model to determine the collision likelihood score. Alternatively, according to some example embodiments, determining the collision likelihood score may include determining the collision likelihood score based on application of the captured sensor data to the collision detection model. In this regard, the captured sensor data may be raw sensory data received from the sensor. Further, according to some example embodiments, determining the collision likelihood score may include determining an estimation of a position of the tip by determining a curvature of the flexible manipulator based on the captured sensor data. According to some example embodiments, the sensor may comprise three sensor nodes, where each of the three sensor nodes being located on a different, respective cross-sectional plane of the flexible manipulator. In this regard, each sensor node may be configured to collect node-level sensor data for inclusion in the sensor data.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits, or solutions described herein should not be thought of as being critical, required, or essential to all embodiments or to that which is claimed herein. Although specific terms are employed herein, they are used in a generic and descriptive sense only and not for purposes of limitation.

What is claimed is:

1. A manipulator apparatus comprising:
   a flexible manipulator comprising a sensor, wherein the flexible manipulator is movable to form a curve;
   a user output device configured to provide sensory outputs to a user; and processing circuitry configured to:
   receive captured sensor data from the sensor during movement of the flexible manipulator;
   determine a collision likelihood score based on application of the captured sensor data to a collision detection model used for position estimation, the collision detection model being based on an empirical data training for the flexible manipulator comprising training sensor data from the sensor and training image data of positions of the flexible manipulator; and
   control the user output device based on the collision likelihood score to provide a collision alert sensory output to the user.

2. The manipulator apparatus of claim 1, wherein the processing circuitry is configured to control the user output device to provide a real-time sonification output to the user based on the collision likelihood score.

3. The manipulator apparatus of claim 1, wherein the flexible manipulator comprises a continuum manipulator controlled via movement of cables.

4. The manipulator apparatus of claim 1, wherein the sensor comprises a fiber Bragg grating (FBG) sensor.

5. The manipulator apparatus of claim 1, wherein the sensor is configured to provide raw sensor data that includes wavelength information.

6. The manipulator apparatus of claim 1 wherein
   the processing circuitry is configured to determine the collision likelihood score based on application of the captured sensor data to the collision detection model, and
   the captured sensor data is the only input to be applied to the collision detection model to determine the collision likelihood score.

7. The manipulator apparatus of claim 1 wherein
   the processing circuitry is configured to determine the collision likelihood score based on application of the captured sensor data to the collision detection model, and the captured sensor data is raw sensory data received from the sensor.

8. The manipulator apparatus of claim 1, wherein
the flexible manipulator comprises a tip, and
the processing circuitry configured to determine the collision likelihood score includes being configured to determine an estimation of a position of the tip by determining a curvature of the flexible manipulator based on the captured sensor data.

9. The manipulator apparatus of claim 1, wherein
the sensor comprises three or more sensor nodes,
each of the sensor nodes is located on a different, respective cross-sectional plane of the flexible manipulator, and
each sensor node is configured to collect node-level sensor data for inclusion in the sensor data.

10. A system for generating a collision detection model for a manipulator apparatus, the system comprising:
a flexible manipulator comprising an sensor, wherein the flexible manipulator is movable to form a curve;
a camera configured capture movement of the flexible manipulator relative to a test collision object;
processing circuitry in communication with the flexible manipulator and the camera, the processing circuitry configured to:
control the flexible manipulator to cause iterations of movement relative to the test collision object with at least one iteration of movement involving a collision between the flexible manipulator and the test collision object;
receive sensor data sets associated with the iterations of movement of the flexible manipulator from the sensor;
receive image data sets associated with the iterations of movement of the flexible manipulator from the camera;
synthesize the sensor data sets with the image data sets to classify the iterations of movement into a collision class and a no collision class; and
generate the collision detection model for use with the flexible manipulator for position estimation in future procedures based on the synthesized data sets and the classifications of the iterations of movement.

11. The system of claim 10, wherein the processing circuitry is configured to generate the collision detection model through implementation of machine learning using a deep neural network, a gradient boosting classifier, or a linear regression model.

12. The system of claim 10, wherein the flexible manipulator comprises a continuum manipulator controlled via movement of cables.

13. The system of claim 10, wherein the sensor comprises a fiber Bragg grating (FBG) sensor.

14. The system of claim 10, wherein the processing circuitry is configured to validate the collision detection model using the synthesized data sets.

15. The system of claim 10, wherein
the sensor comprises three or more sensor nodes,
each of the sensor nodes is located on a different, respective cross-sectional plane of the flexible manipulator, and
each sensor node is configured to collect node-level sensor data for inclusion in the sensor data sets.

16. A method for generating a collision detection model for a manipulator apparatus, the method comprising:
controlling a flexible manipulator to cause iterations of movement relative to a test collision object with at least one iteration of movement involving a collision between the flexible manipulator and the test collision object;
receiving sensor data sets associated with the iterations of movement of the flexible manipulator from a sensor, wherein the flexible manipulator comprises the sensor;
receiving image data sets associated with the iterations of movement of the flexible manipulator from a camera, the camera being remote from the flexible manipulator;
synthesizing, by processing circuitry, the sensor data sets with the image data sets to classify the iterations of movement into a collision class and a no collision class; and
generating a collision detection model for use with the flexible manipulator for position estimation in future procedures based on the synthesized data sets and the classifications of the iterations of movement.

17. The method of claim 16, wherein the generating the collision detection model includes implementation of a classifier such as gradient boosting classifier.

18. The method of claim 16, wherein the sensor comprises a fiber Bragg grating (FBG) sensor.

19. The method of claim 16, wherein the generating the collision detection model includes validating the collision detection model using the synthesized data sets.

20. The method of claim 16, wherein
the sensor comprises three or more sensor nodes,
each of the sensor nodes being located on a different, respective cross-sectional plane of the flexible manipulator, and
each sensor node being configured to collect node-level sensor data for inclusion in the sensor data sets.

* * * * *